United States Patent
Pobitschka (10) Patent No.: US 9,238,096 B2
(45) Date of Patent: Jan. 19, 2016

(54) METHOD AND DEVICE FOR SEPARATING BLOOD USING A CENTRIFUGE

(76) Inventor: Walter Pobitschka, Bad Homburg (DE)

( * ) Notice: Subject to any disclaimer, the term of this patent is extended or adjusted under 35 U.S.C. 154(b) by 1268 days.

(21) Appl. No.: 13/062,899

(22) PCT Filed: Sep. 13, 2009

(86) PCT No.: PCT/DE2009/001273
§ 371 (c)(1),
(2), (4) Date: May 26, 2011

(87) PCT Pub. No.: WO2010/028638
PCT Pub. Date: Mar. 18, 2010

(65) Prior Publication Data
US 2011/0224062 A1    Sep. 15, 2011

(30) Foreign Application Priority Data
Sep. 12, 2008   (DE) .......................... 10 2008 047 068

(51) Int. Cl.
*A61M 1/36*      (2006.01)
*A61M 1/02*      (2006.01)

(52) U.S. Cl.
CPC .......... *A61M 1/3693* (2013.01); *A61M 1/0209* (2013.01); *A61M 1/0272* (2013.01); *A61M 2202/0462* (2013.01)

(58) Field of Classification Search
CPC ............ A61M 1/0209; A61M 1/0272; A61M 1/3693; A61M 2202/0462
USPC .......... 494/5, 43, 44, 45, 60, 62, 63; 422/533, 422/548
See application file for complete search history.

(56) References Cited

U.S. PATENT DOCUMENTS

| 35,804 A | 7/1862 | Woodworth |
| 4,268,393 A * | 5/1981 | Persidsky et al. ............... 494/21 |

(Continued)

FOREIGN PATENT DOCUMENTS

| DE | 27 41 398 A1 | 3/1978 |
| DE | 69819689 | 9/2004 |

(Continued)

OTHER PUBLICATIONS

International Preliminary Report on Patentability for International Application No. PCT/DE2009/001273, mailed May 12, 2011.

(Continued)

*Primary Examiner* — Timothy Cleveland
(74) *Attorney, Agent, or Firm* — Alston & Bird LLP (57) ABSTRACT

The invention relates to a method and a device for separating blood using a centrifuge in order to obtain different blood fractions. The aim of the invention is to eliminate the risk of contamination during the supply of blood and the removal of blood fractions. To achieve this, the separation container is filled with blood via a feed connection that can be aseptically connected to the container, the relevant blood fraction is removed from the separation container via a removal connection that can be aseptically connected to the container and both the feed device and the removal device form a respective closed system during the sterile connection to the separation container. The separation container (4) has at least one feed connection (5, 6) that can be aseptically connected to the container and at least one removal connection (7) that can be aseptically connected to the container, to which hermetically sealed feed and removal devices (8, 9, 10) can be aseptically attached in a sterile manner.

15 Claims, 4 Drawing Sheets

(56) References Cited

U.S. PATENT DOCUMENTS

| | | | |
|---|---|---|---|
| 4,617,009 A | 10/1986 | Öhlin et al. | |
| 4,850,952 A | 7/1989 | Figdor et al. | |
| 6,068,970 A | 5/2000 | Hosono et al. | |
| 6,197,579 B1 * | 3/2001 | Van Vlasselaer et al. | 210/782 |
| 6,733,433 B1 | 5/2004 | Fell | |
| 2004/0167004 A1 * | 8/2004 | Jorgensen et al. | 494/37 |
| 2008/0103428 A1 * | 5/2008 | Delaronde-Wilton | 604/6.03 |
| 2008/0248938 A1 * | 10/2008 | Chammas | 494/10 |

FOREIGN PATENT DOCUMENTS

| | | |
|---|---|---|
| DE | 20 2007 007 136 | 9/2007 |
| DE | 10 2008 035 835 | 2/2010 |
| DE | 10 2008 035 837 | 2/2010 |
| GB | 1 591 989 | 9/1977 |
| GB | 1 591 989 A | 7/1981 |
| WO | WO 99/45851 | 9/1999 |
| WO | WO 00/07642 | 2/2000 |
| WO | WO 00/38762 | 7/2000 |
| WO | WO 2005/039773 | 5/2005 |

OTHER PUBLICATIONS

International Search Report for International Application No. PCT/DE2009/001273.

* cited by examiner

METHOD AND DEVICE FOR SEPARATING BLOOD USING A CENTRIFUGE

CROSS-REFERENCES TO RELATED APPLICATIONS

The application is a national stage entry of PCT/DE2009/001273 filed Sep. 13, 2009, which application claims priority to German Patent Application DE 10 2008 047 068.6 filed Sep. 12, 2008, both of which are hereby incorporated by reference herein in their entireties.

BACKGROUND OF THE INVENTION

1. Field of the Invention

The invention relates to a method for separating blood using a centrifuge in order to obtain different blood fractions.

Furthermore, the invention relates to a device for separating blood using a centrifuge comprising a rotor and at least one separation container, in particular to carry out the method.

2. Description of Related Art

Blood can be separated into different blood fractions by means of a centrifuge in that the centrifuge is rapidly rotated at defined revolutions and over a defined period of time. After the centrifugation, the blood in the separation container has changed. The individual constituents have separated into blood plasma, which consists primarily of protein and water, white blood corpuscles and solid blood constituents.

The preparation of the blood before and after the separation process is very time consuming and is generally done in the atmosphere—that is, in an open system that is, by definition, contaminated. It is precisely in the case of umbilical cord blood preparation, but also in the case of other kinds of blood, that the contamination is not desired. For more comprehensive preparations, the white blood corpuscles are the most relevant.

Working on the basis of the prior art known from practical application, the object of the invention is to provide a method and a device of the type under discussion that eliminates the risk of contamination during the filling with blood and during the extraction of blood fractions.

SUMMARY OF VARIOUS EMBODIMENTS

The aforesaid object is achieved with a method exhibiting the features of various embodiments described herein. Correspondingly a method of the type under discussion is configured in such a way that the separation container is filled with blood via a feed port, which can be aseptically connected to said separation container; that the relevant blood fraction is extracted from the separation container via an extraction port, which can be aseptically connected to said separation container; and that the feed device and the extraction device form a respective closed system during the sterile connection to the separation container.

The aforementioned object is achieved with a device exhibiting the features of various embodiments described therein. Correspondingly a device of the type under discussion is configured in such a way that the separation container has at least one feed port, which can be aseptically connected to said separation container, and at least one extraction port, which can be aseptically connected to said separation container, to which the hermetically sealed feed and extraction devices can be aseptically attached.

It has been recognized from the prior art known from practical experience that the risk of contamination can be greatly reduced if the filling of the separation container, which is outwardly sealed in the well-known manner and which is located in the centrifuge, and the extraction from this separation container of the centrifuge are performed with the exclusion of the atmosphere. The invention recognizes that it is possible to exclude contact with the atmosphere, if a closed system is formed between the feed device and the separation container and between the extraction device and the separation container, and/or if the aseptically connectable ports provide such a condition that the specifically designed and hermetically sealed feed and extraction devices can be aseptically attached. It is apparent that the inventive approach reduces the risk of contamination.

According to a preferred embodiment two feed devices could be connected to two feed ports for feed purposes. This strategy offers the possibility of also delivering, in addition to blood, auxiliary agents to improve the centrifugation. Hence, it would also be possible to aseptically weld a feed device for the anticoagulated blood and a feed device for the hydroxyethyl starch solution (hereinafter referred to as HES) to the respective feed port. The HES promotes the sedimentation of erythrocytes or rather red blood corpuscles that are to settle out.

While the separation container is being filled with blood, it would be advantageous to simultaneously attach the feed device for the HES. This strategy has the advantage that the sterile air, which is displaced from the separation container by the blood, can escape into the feed device for the HES. Moreover, while the blood is injected by means of the feed device for the HES, a negative pressure could also be generated, and the sterile air could be actively drawn in from the separation container. The displaced or aspirated sterile air could flow into a supply container of the feed device for the HES or could be released into a pressure-compensating device. This approach ensures that the sterile air flows into the supply container of the feed device for the HES in such a way that it bypasses the HES. To this end, during the delivery of sterile air, the HES-containing area of the flexible supply container of the feed device for HES could be moved away from the inlet point to the supply container. For example, the supply container, which exists as a flexible bag, could be bent away, so that the displaced sterile air flows in without flowing through the HES. In the case of the HES addition, sterile air displaced by the HES solution could flow just as well into the feed device for blood.

This particular design of the feed device could enable a volume-accurate addition of the blood. The same applies to the addition of the HES solution. The necessary amount of HES could be pre-calculated in consideration of the amount of injected blood.

When the filling with blood and in some cases additionally with HES has been completed, the sterile disconnection between the feed device and the separation device could occur. This step could be achieved by the well-known sterile welding method. In any event it is absolutely imperative that the separation container be sealed off from the outside world.

The separation container has to absorb many forces during centrifugation and for this reason has a shell structure for stabilization. The shell structure could comprise a cover plate that exhibits recesses for accommodating the feed ports and optionally the extraction port. After the disconnection, the freely downward-extending ports can be brought into the recesses, so that there are no breakdowns during the centrifugation. Centrifugation occurs in exact time phases, in particular at an acceleration of 1,500 g.

The separation container could hold two containers that are flow-connected to each other. During the centrifugation, the blood fraction of white blood corpuscles collects predominantly inside the flow connection between the containers. This state can be detected by the color of the substance. In addition, an optical reader could be used to determine the phase boundary. When the phase boundary is recognized, the flow connection that is present as a plastic hose could be disconnected by means of a hose clamp at the phase boundary between the blood fraction of the solid blood constituents and the blood fraction of white blood corpuscles. The hose clamp could be applied by means of the open regions of the shell structure. The separation container itself is sealed air tight and can be connected to the systems, which are also closed, only by way of the ports. The design of the flow connection per plastic hose is advantageous because of the ease with which it can be disconnected. At the same time the hose clamp can be positioned exactly at the point, where the phase boundary runs between the erythrocytes and the leukocytes. This site may vary from patient to patient. Experience has demonstrated that in forming the separation container with the plastic hose the yield is very high. In addition, the extraction of blood fractions does not have to be limited to the leukocytes. Rather plasma may also be aspirated from the top internal container in order to reach a standardized volume. The standardized volume can be used for cryopreservation, for which there are narrow specifications for the procedure.

According to a second embodiment, there could also be an additional feed port for an additional feed device—in this case, for delivering a filling material to reduce the volume of the container that holds the centrifuged erythrocytes. In order to form the phase boundary inside the flow connection, preferably at the lower end of the flow connection, between the containers, the volume of the lower container could be changed. The change relates to the fact that there is a difference between the fill volume of blood and the erythrocytes therein and the pack volume of the centrifuged erythrocytes. The future pack volume can be calculated by means of the hematocrit value, known from each blood sample, and by means of the fill volume of the blood. The fill volume can be determined either by using the value of the known volume of the feed device (or more specifically the bag volume) or by using a scaled feed device, which results in the amount of drawn blood that then yields the fill volume. As an alternative, the separation container can also be scaled. The volume of the container of the separation container, which is provided for holding the centrifuged erythrocytes, could be decreased by filling with inert beads. After determining the fill volume in the separation container and after calculating the pack volume by means of the hematocrit value, the percentage, to which the lower container will be filled with the centrifuged erythrocytes, can be estimated. The expected pack volume of erythrocytes usually falls below the volume of the lower container of the separation container. In order to form at this point the phase boundary in the flow connection and not in the lower container, the container could be filled with so many beads that the volume is filled beyond the expected pack volume. During centrifugation the beads collect on the bottom of the container under discussion due to their comparatively high weight, and over them the erythrocytes. The phase boundary develops, as desired, in the flow connection, at its lower end. Therefore, the leukocytes or more specifically the so-called buffy coat, consisting of leukocytes and thromocytes, collect optimally in the flow connection.

In order to extract the blood fraction of white blood corpuscles from the plastic hose, an extraction device could be aseptically connected to the extraction port. The extraction device could exhibit a configuration described in DE 10 2008 035 835, wherein the interior of the extraction device has an internal line. After the two closed systems have been connected to form a total closed system, this inner line could be inserted into the separation container or more specifically into the flow connection, in order to extract the blood fraction of white blood corpuscles. The interior of the extraction device could have a syringe that extracts the relevant blood fraction with one plunger stroke and then transfers it into the hermetically sealed extraction device. The interior of the extraction device could have, for example, a container to hold the blood fraction.

After the blood fraction of white blood corpuscles has been removed from the separation container, the extraction device could also be aseptically disconnected, so that it is ensured that in any event the extraction device does not make contact with the atmosphere.

With respect to the construction of the device, the first step is to stress the special configuration of the separation container according to a preferred embodiment. In the interior of the separation container the separation container could comprise two containers that are flow-connected to each other. When the separation container is in quiescent position in the rotor bowl of the rotor, the first container with a funnel-shaped bottom could be disposed above the second container. The flow connection could be attached to the funnel outlet in the form of a plastic hose that empties into the second container. The funnel-shaped bottom facilitates the delivery of blood from the first to the second container. As an alternative to the above-described configuration, there could also be provided a ring-shaped separation container that extends about the rotor axis and has a cross section that consists of two expansions and a central constriction. Furthermore, the ring-shaped separation container could also be segmented into a plurality of chambers.

Since the blood fraction of white blood corpuscles is relevant for the subsequent preparation steps, and these white blood corpuscles are collected predominantly in the flow connection after the centrifugation, the extraction port could be in alignment with the flow connection. This feature makes it much easier to insert an inner line of the extraction device after the sterile connecting to the extraction port.

The stability of the separation container is not especially high because of the soft plastic hose as the flow connection. Therefore, the separation container could be disposed inside a shell structure. The shell structure could have open areas, through which a hose clamp can be fastened on the flow connection or more specifically the plastic hose. The hose clamp is supposed to prevent the phases that were obtained after the centrifugation—that is, the red blood corpuscles in the lower internal container and the white blood corpuscles in the plastic hose or more specifically in the flow connection—from mixing.

As stated above with respect to the method, it would be possible to provide, according to a first embodiment, two feed ports, which are spaced at a distance from the extraction port and are intended for blood, on the one hand, and for the hydroxyethyl starch solution HES, on the other hand. In the specific case it would be possible to use a feed device that comprises a syringe, sitting inside a sleeve and comprising a tube and a plunger that exhibits a passage opening. If there are additionally shut-off devices at the tube and the plunger end, then it is possible to draw in and eject multiple times, during which the shut-off devices are either alternatively closed or opened, as needed. Consequently it is possible to work in both directions, because the suction is not necessarily a function of pulling the plunger out of the tube. Owing to the passage opening in the plunger the suction process can also take place by pushing the plunger in; only the correct shut-off device has to be opened—that is, the shut-off device on the suction side. Furthermore, it is important that aseptically connectable ports descend downwards from the sleeve. Additional possibilities for closed donor systems with downwards descending and aseptically connectable ports are apparent from DE 10 2008 035 837.

According to a second embodiment, the separation container could have an additional aseptically connectable feed port, to which an additional hermetically sealed feed device for a filling material, in particular inert beads, can be attached in order to reduce the volume in the container that is provided for holding the centrifuged erythrocytes. The feed devices could be operated subject to gravitational force and could have in each case a metering shut-off device so that a volume-accurate metering can be performed.

According to an additional embodiment for an extraction device with the above-described inner line, which can be applied in the flow connection, this inner line could be connected to a syringe that is situated inside a sleeve and comprises a tube and a plunger, which has a passage opening. The inner line can be handled via a bellows of the sleeve; for this purpose the aseptically connected ports form the guide for the inner line. Then the syringe is handled by way of the shut-off devices, as described with respect to the feed device.

One important aspect of the invention is that the feed device and the extraction device are in themselves closed systems that also form together with the separation container a closed system during the aseptic connection to the corresponding port of the separation container. As a result, contamination is no longer a factor

BRIEF DESCRIPTION OF THE SEVERAL VIEWS OF THE DRAWINGS

At this point there are a plethora of possibilities for configuring and further developing the teaching of the present invention in an advantageous way. To this end, reference is made, first of all, to the various embodiments described herein and secondly to the following description of two embodiments of the invention with reference to the drawings. The description of the inventive embodiments presented herein also includes an explanation of the generally preferred configurations and further developments of the teaching. In the drawing

DETAILED DESCRIPTION

FIGS. 1 to 3, 5 and 6 show a device for separating blood using a centrifuge (shown in FIG. 1) with a rotor 2 and herein four rotor bowls 3. Each rotor bowl 3 has a separation container 4. The drawing does not show the rotor shaft or other design features.

Figure 1:
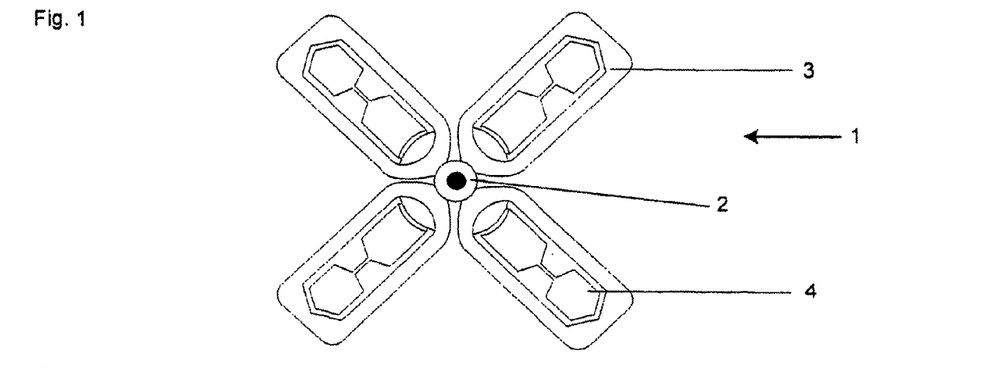
FIG. 1 is a diagrammatic sketch of a top view of the centrifuge in its operating position using the inventive device with a separation container.
Figure 2:
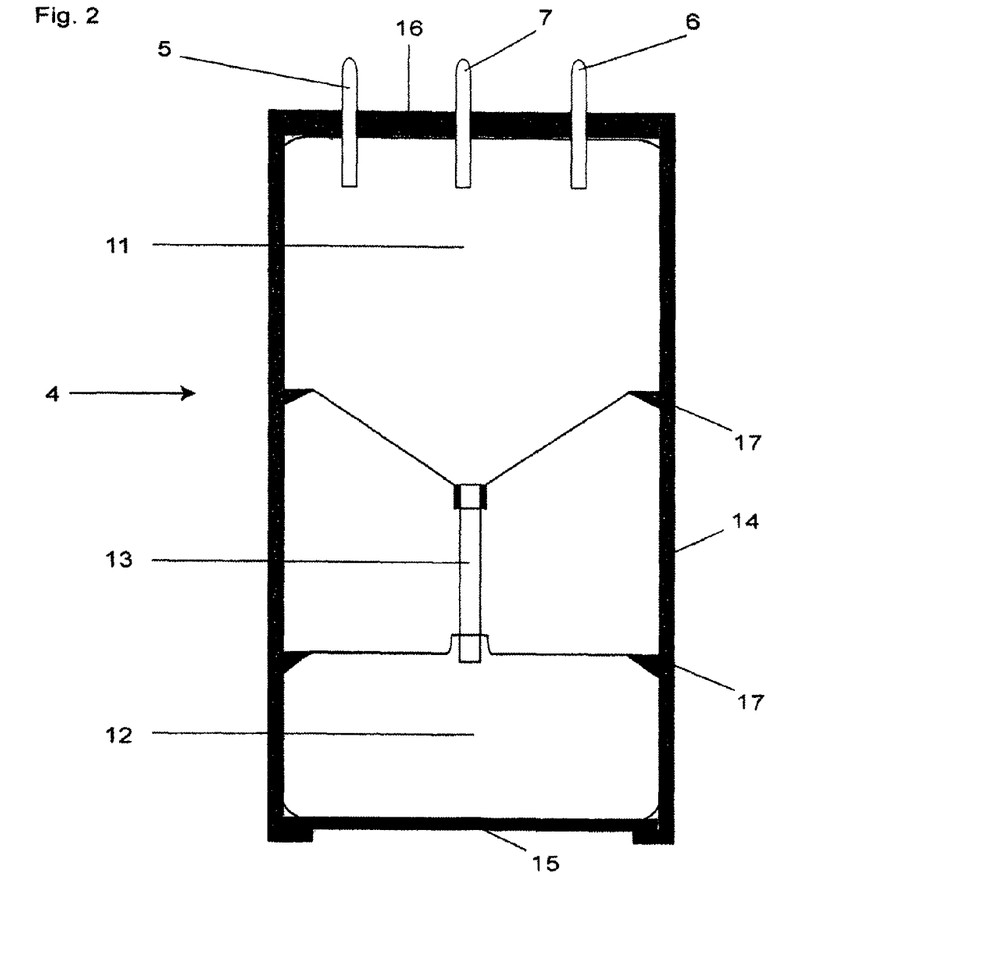
FIG. 2 is a schematic drawing, enlarged, of a detail from FIG. 1, regarding a first exemplary embodiment of the inventive device with two feed ports and one extraction port.

The first exemplary embodiment of the invention provides that the separation container 4 has two feed ports 5, 6, which can be aseptically connected to the separation container, and an extraction port 7, which can be aseptically connected to the separation container, to which the hermetically sealed feed and extraction devices 8, 9, 10 can be aseptically attached.

The separation container 4 comprises two containers 11, 12, which are flow-connected to each other. The bottom of the container 11 is configured as a funnel. In order to form the flow connection 13, there is a flexible PVC hose that is seal-welded to the containers 11, 12. The extraction port 7 aligns with the flow connection 13. The separation container 4 is disposed inside the shell structure 14 comprising a base plate 15 and a cover plate 16. The base plate 15 and the cover plate 16 are securely connected to the shell structure. The shell structure 14 has reinforcements 17 that fulfill the function of inner shoulders or stabilizers.

The shell structure 14 has openings (not illustrated here), through which the hose clamp 18 (shown in FIG. 6) can be fastened on the flow connection 13.

Figure 3:
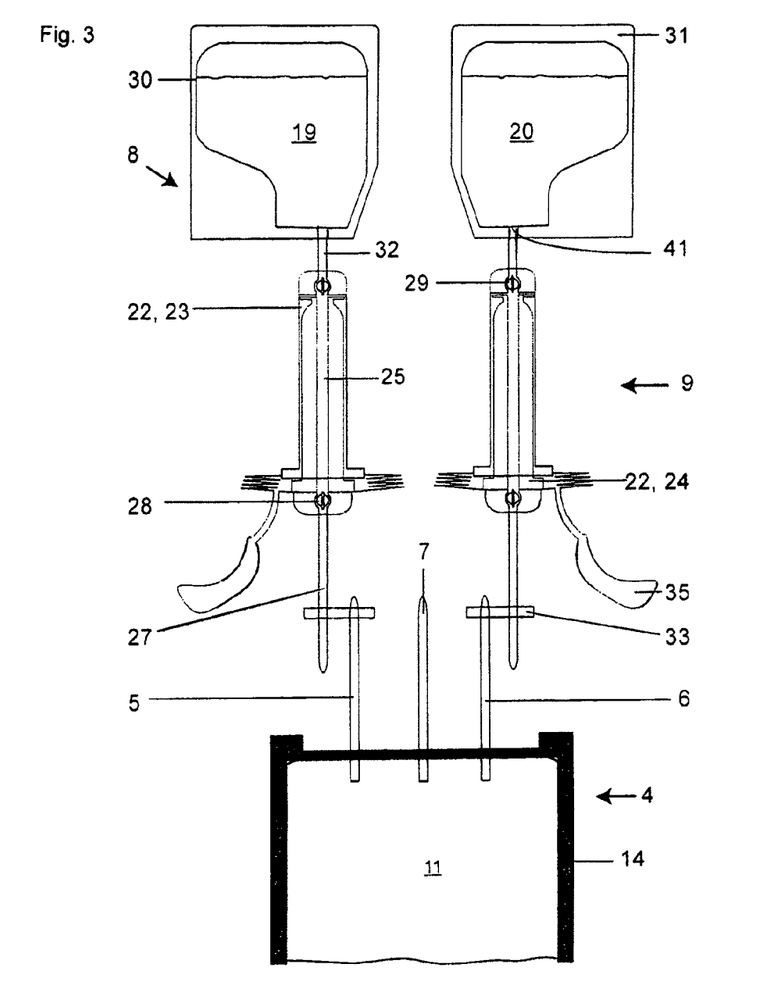
FIG. 3 is a schematic drawing, reduced in size, of the subject matter from FIG. 2 with two aseptically connected feed devices.

FIG. 3 shows that the umbilical cord blood with an anticoagulant 19 flows through the feed device 8 into the separation container 4, and through the feed device 9 a hydroxyethyl starch solution 20 flows, hereinafter referred to as HES.

The feed devices 8, 9 have a syringe 22, which sits inside a sleeve 21 and comprises a tube 23 and a plunger 24, which has a passage opening 25. The reference numeral 35 denotes a pressure-compensating device, into which the displaced sterile air can escape.

From the sleeve 21 aseptically connectable ports 27 descend, which can be opened and closed by shut-off devices 28, 29 in the form of two way stopcocks. The shut-off devices 28, 29 serve to achieve the transfer of the umbilical cord blood with anticoagulant 19 from the supply container 30 to the separation container 4 and to achieve the transfer of the HES 20 from the supply container 31 to the separation container 4.

The respective substance 19, 20 is drawn into the respective feed device 8, 9 through the syringe 22. The respective substance 19, 20 can be transferred into the separation container 4 through the passage opening 25. The tube-sided port 32 and the plunger-sided port 27 extend downwards from the sleeve 21 and are tightly connected to it.

The operating principle of the feed devices 8, 9 is explained below.

In the present embodiment the supply containers 30, 31 and the syringe 22 with the sleeve 21 are pre-assembled. The plunger-sided port 27 is attached to the feed port 5, 6 of the separation container 4.

The shut-off device 29 of the tube-sided port 32 is opened prior to the—in this case, volume-accurate—suction process, and the shut-off device 28 of the plunger-sided port 27 of the syringe 22 is closed. The syringe 22 or more specifically the plunger 24 and the shut-off devices 28, 29 are actuated by means of the sleeve 21 from the outside.

During the suction process the tube 23 of the syringe 22 is filled with the substance 19, 20.

Prior to passing the substance 19, 20 from the syringe 22 to the separation container 4, the shut-off device 29 of the tube-sided port 32 is closed, and the shut-off device 28 of the plunger-sided port 27 is opened. In order to pass the substance 19, 20 even further, the plunger 24 of the syringe 22 is pushed into the tube 23. As a result, the tube 23 empties via the passage opening 25 and the plunger-sided port 27 and its opened shut-off device 28 into the feed port 5, 6 and then into the separation container 4. Reference numeral 33 denotes the sterile connection between the feed ports 5, 6 and the plunger-sided ports 27.

Figure 4:
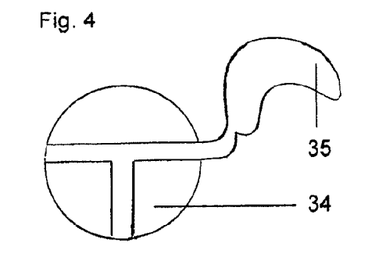
FIG. 4 is a sketch of an alternative removal of the displaced sterile air from the separation container.

FIG. 4 shows, as an alternative to the shut-off device 29, 28 in the form of a two way stopcock, a three-way stopcock 34 with a pressure-compensating device 35 for accommodating the displaced sterile air from the separation container 4. The feed devices 8, 9 and the extraction device 10 also have a pressure-compensating device 35 for buffering the variations in volume.

Figure 5:
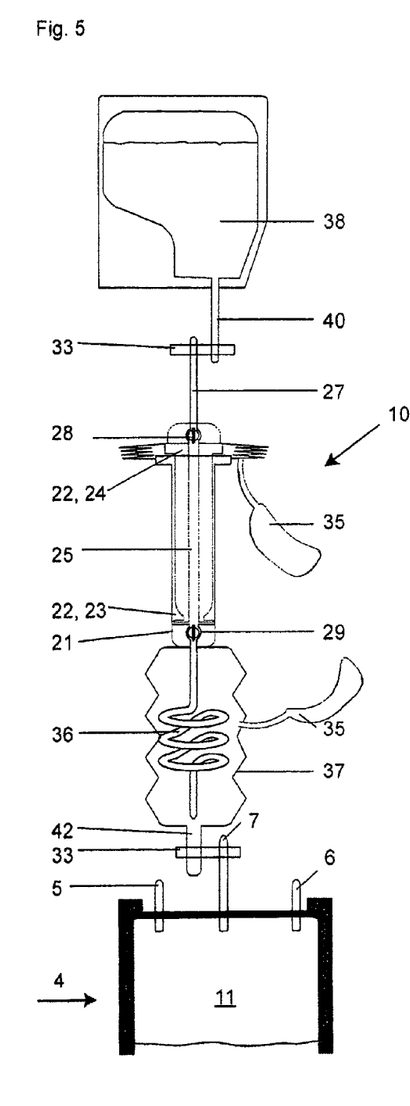
FIG. 5 is a schematic drawing, reduced in size, of the subject matter from FIG. 2 prior to the aseptic connection to an extraction device.
Figure 6:
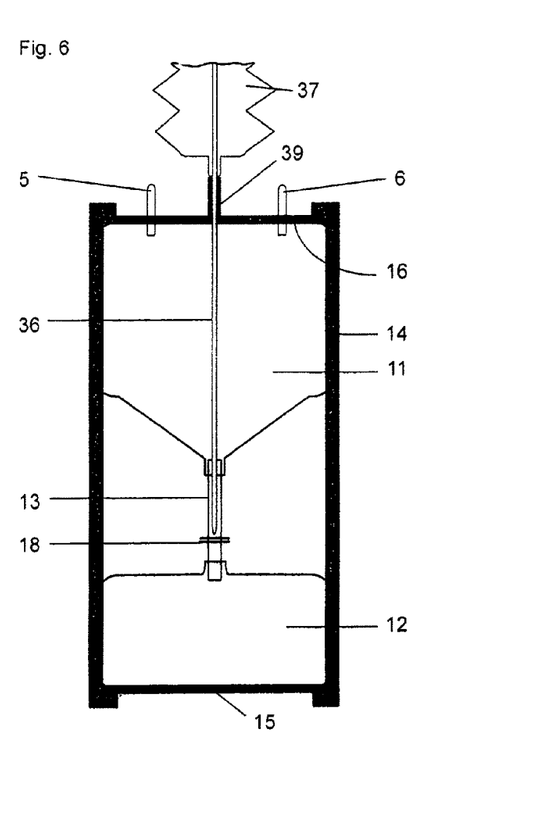
FIG. 6 is a schematic drawing, reduced in size, of the subject matter from FIG. 2 with the aseptically connected extraction device and the hose clamp as well as the inserted inner line.

FIGS. 5 and 6 relate to the extraction process after the centrifugation. The feed devices 8, 9 are already aseptically welded; the feed ports 5, 6 have become a little shorter. The extraction device 10 has an inner line 36 that can be applied through the extraction port 7 into the flow connection 13. The inner line 36 is disposed inside a bellows 37 with a pressure-compensating device 35 and is aseptically connected to the sleeve 21 with a syringe 22 comprising a tube 23 and a plunger 24 that has a passage opening 25. The syringe 22 of the extraction device 10 works according to the same principle as the syringe of the feed devices 8, 9. In this case, too, the shut-off devices 28, 29 are provided. The only difference is that the tube 23 points toward the separation container 4, where, in addition to the corresponding actuation of the shut-off devices 28, 29, the suction process takes place before the extracted blood fraction of white blood corpuscles is emptied via the passage opening 25 of the plunger 24 into the collapsed bag 38. The bag 38 is also aseptically connected to the plunger-sided port 27 by way of the port 40 of the bag.

In FIG. 5 the inner line 36 is still wound up. In FIG. 6 the inner line 36 is extracted and inserted into the flow connection 13, in which the relevant white blood corpuscles have collected. In addition, FIG. 6 also shows a stabilizing sleeve 39 at the extraction port 7.

The feed devices 8, 9 and the extraction device 10 are closed systems, just like the separation container 4. During sterile connection to the corresponding ports 5, 6, 7 of the separation container 4, the feed devices 8, 9 and the extraction device 10 also form together with said separation container a closed system.

The following process steps can be performed with this device.

Umbilical cord blood with an anticoagulant 19 and the HES 20 is fed into the separation container 4 by way of the two feed devices 8, 9. At the same time sterile air from the separation container 4 flows into the feed device 9 for HES 20 and, in particular, as far as into the supply container 31. In FIG. 4 a three-way stopcock 34 with a pressure-compensating device 35 is provided as an alternative. The displaced sterile air flows into the supply container 31 of the feed device 9 for HES 20, so that it flows past the HES 20. During the delivery of the sterile air, the HES-containing area of the flexible supply container 31 of the feed device 9 for HES 20 is moved away from the inlet point 42 into the supply container 31. The next step involves a volume-accurate addition of both substances 19, 20. The required amount of HES 20 is calculated in consideration of the added amount of umbilical cord blood with an anticoagulant 19. Having filled the separation container 4, the feed devices 8, 9 are aseptically disconnected. In order to extract the blood fraction of white blood corpuscles from the flow connection 13, the extraction device 10 is aseptically connected to the extraction port 7. The inner line 36, disposed in the interior of the extraction device 10, is inserted into the flow connection 13, in order to extract the blood fraction of white blood corpuscles. After the blood fraction of white blood corpuscles has been extracted through repeated aspiration and ejection from the separation container, the extraction port 7 and the port 42 of the bellows 37 of the extraction device 10 are aseptically disconnected.

The second embodiment (shown in FIG. 7) of the device according to the invention relates to a third aseptically connectable feed port 43, to which an additional hermetically sealed feed device 44 for feeding inert beads 45 is attached. The inert beads 45 are needed to reduce the volume in the container 12, so that the phase boundary between the erythrocytes, which are supposed to collect predominantly in the container 12 after the centrifugation, and the leukocytes, which are supposed to collect exclusively in the flow connection 13 after the centrifugation, acquires a predefined position on the lower end of the flow connection 13.

Figure 7:
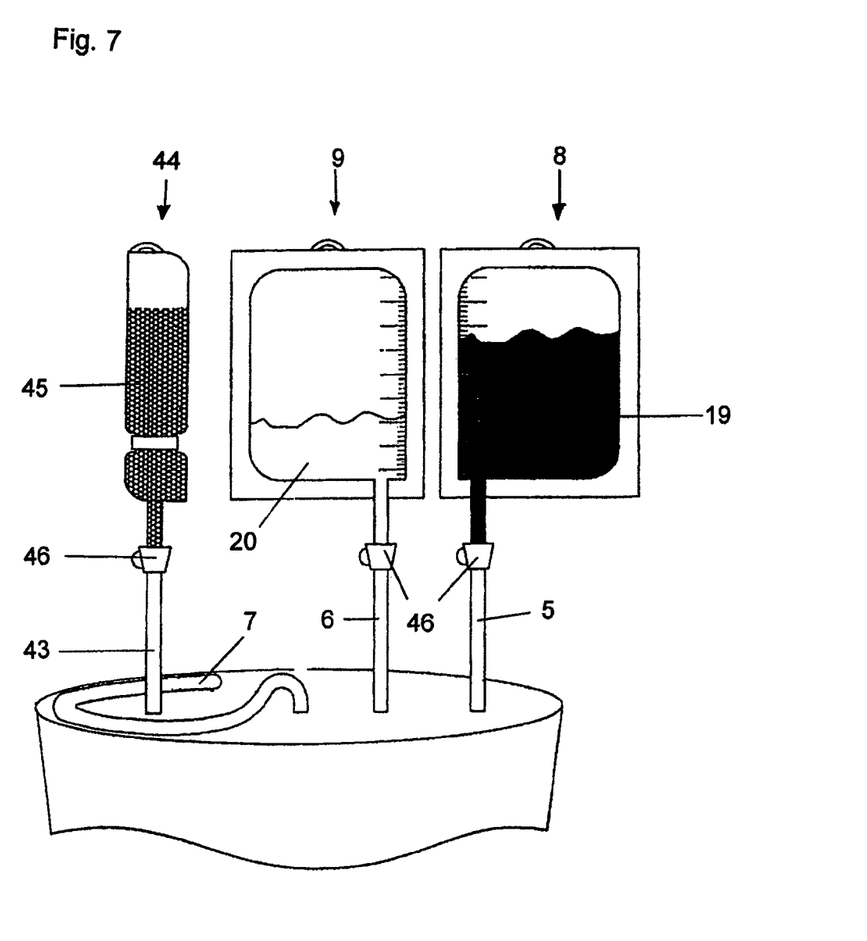
FIG. 7 is a schematic drawing of the feed devices at the separation container, according to a second exemplary embodiment of the device according to the invention.

All three feed devices 8, 9, 44 are operated herein subject to gravitational force. A metering shut-off device 46 is provided for metering the blood 19, HES 20 and inert beads 45.

With respect to features that are not shown in the figures, reference is made to the general part of the specification.

Finally it must be pointed out that the teaching according to the invention is not limited to the above-described embodiment.

The invention claimed is:

1. A device for separating blood using a centrifuge, said device comprising:
   a rotor and at least one separation container, wherein the at least one separation container has at least one feed port aseptically connected to the at least one separation container, and at least one extraction port aseptically connected to the at least one separation container;
   wherein the at least one separation container comprises an upper container and a lower container that are flow-connected to each other via a flow connection;
   wherein a flexible PVC hose is configured to define the flow connection;
   wherein during centrifugation, the upper container is configured to be disposed radially inward with respect to the lower container;
   wherein at least the lower container is reinforced such that the lower container is configured to maintain a predetermined volume during centrifugation; and
   wherein during the centrifugation, the flow connection between the upper container and the lower container is configured to collect at least a portion of a blood fraction of white blood corpuscles.

2. The device as claimed in claim 1, wherein the extraction port aligns with the flow connection.

3. The device as claimed in claim 1, wherein the at least one separation container is disposed inside a shell structure, and wherein the shell structure is connected to at least the lower container such that at least the lower container is reinforced by the shell structure.

4. The device as claimed in claim 3, wherein the shell structure is created in such a way that a hose clamp can be fastened on the flow connection.

5. The device as claimed in claim 1, wherein the at least one feed port comprises two feed ports which are spaced at a distance from the at least one extraction port and a first feed port of the two feed ports is intended for blood and a second feed port of the two feed ports is intended for hydroxyethyl starch solution (HES).

6. The device as claimed in claim 1, further comprising a hermetically sealed feed device attached to one of the at least one feed ports, wherein the feed device comprises a syringe sitting inside a sleeve and comprising a tube and a plunger that exhibits a passage opening.

7. The device as claimed in claim 6, wherein aseptically connectable ports extend downwards from the sleeve and can be opened and closed by means of shut-off devices.

8. The device as claimed in claim 1, further comprising a hermetically sealed extraction device attached to one of the at least one extraction ports, wherein the extraction device has an inner line, which can be applied in the flow connection and in the container and which is connected to a syringe that is situated inside a bellows and comprises a tube and a plunger, which has a passage opening.

9. The device as claimed in claim 1, further comprising a hermetically sealed feed device attached to one of the at least one feed ports and a hermetically sealed extraction device attached to one of the at least one extraction ports, wherein the feed device and the extraction device are closed systems and also form together with the at least one separation container a closed system during the aseptic connection to the corresponding ports of the at least one separation container.

10. The device as claimed in claim 1, wherein the at least one separation container has an additional aseptically connectable feed port, wherein the device further comprises a hermetically sealed feed device for a filling material including inert beads attached to the additional aseptically connectable feed port in order to reduce the volume in the at least one separation container.

11. The device as claimed in claim 1, further comprising a hermetically sealed feed device attached to one of the at least one feed ports, wherein the feed device is configured to be operated subject to gravitational force and wherein the feed device further comprises a metering shut-off device.

12. A device for separating blood using a centrifuge, said device comprising:
a rotor and at least one separation container, wherein the at least one separation container has at least one feed port aseptically connected to the at least one separation container, and at least one extraction port aseptically connected to the at least one separation container, and a hermetically sealed extraction device attached to one of the at least one extraction ports;
wherein the at least one separation container comprises an upper container and a lower container that are flow-connected to each other via a flow connection;
wherein during centrifugation, the upper container is configured to be disposed radially inward with respect to the lower container;
wherein at least the lower container is reinforced such that the lower container is configured to maintain a predetermined volume during centrifugation; and
wherein during the centrifugation, the flow connection between the upper container and the lower container is configured to collect at least a portion of a blood fraction of white blood corpuscles; and
wherein the extraction device comprises an inner line, which is configured to connect to the flow connection such that the inner line is configured to extract the blood fraction of white blood corpuscles from the flow connection.

13. The device as claimed in claim 1, wherein the upper container is reinforced such that the upper container is configured to maintain a predetermined volume during centrifugation.

14. The device as claimed in claim 1, wherein the lower container contains one or more inert beads.

15. The device as claimed in claim 2, further comprising a hermetically sealed extraction device attached to one of the at least one extraction ports, the extraction device including an inner line configured to extend at least from the extraction port to the flow connection, and wherein the inner line is disposed at least partially within the flow connection.

* * * * *